(12) United States Patent
Ito et al.

(10) Patent No.: US 8,487,273 B2
(45) Date of Patent: Jul. 16, 2013

(54) MICROCHIP AND PARTICULATE FRACTIONAL COLLECTION APPARATUS

(75) Inventors: Tatsumi Ito, Kanagawa (JP); Masaya Kakuta, Tokyo (JP); Shingo Imanishi, Kanagawa (JP); Nao Nitta, Tokyo (JP); Koji Futamura, Kanagawa (JP); Toru Takashimizu, Kanagawa (JP); Koji Ashizaki, Tokyo (JP); Motohiro Furuki, Tokyo (JP)

(73) Assignee: Sony Corporaiton, Tokyo (JP)

( * ) Notice: Subject to any disclaimer, the term of this patent is extended or adjusted under 35 U.S.C. 154(b) by 45 days.

(21) Appl. No.: 13/315,052

(22) Filed: Dec. 8, 2011

(65) Prior Publication Data
US 2012/0153185 A1    Jun. 21, 2012

(30) Foreign Application Priority Data
Dec. 17, 2010   (JP) .................................. 2010-282167

(51) Int. Cl.
*G01N 21/64*    (2006.01)
(52) U.S. Cl.
USPC ..................................................... 250/458.1
(58) Field of Classification Search
USPC .................................................... 250/458.1
See application file for complete search history.

(56) References Cited

U.S. PATENT DOCUMENTS

| | | | |
|---|---|---|---|
| 2007/0240495 A1 | 10/2007 | Hirahara | |
| 2008/0311005 A1* | 12/2008 | Kim et al. | 422/82.05 |

FOREIGN PATENT DOCUMENTS

| | | |
|---|---|---|
| JP | 2003-274924 | 9/2003 |
| JP | 2004-113223 | 4/2004 |
| JP | 2005-538727 | 12/2005 |
| JP | 2006-29824 | 2/2006 |
| JP | 2007-330201 | 12/2007 |
| WO | 2004-025266 | 3/2004 |
| WO | 2005-121767 | 12/2005 |

\* cited by examiner

*Primary Examiner* — Kiho Kim
(74) *Attorney, Agent, or Firm* — K&L Gates LLP

(57) ABSTRACT

A microchip includes a sample liquid feed channel permitting a sample liquid containing particulates to flow through, at least one pair of sheath liquid feed channels configured to merge to the sample liquid feed channel from both sides thereof for permitting a sheath liquid to flow through surrounding the sample liquid, a merging channel connected to the sample liquid feed channel and the one pair of the sheath liquid feed channels for permitting the sample liquid and the sheath liquid to merge and flow through the merging channel, a vacuum suction unit for drawing into the particulate subject to collection, connected to the merging channel, and at least one pair of discharge channels formed on both sides of the vacuum suction unit for permitting to flow through from the merging channel.

14 Claims, 17 Drawing Sheets

| PARTICLE No. | FSC | SSC | FL1 | FL2 | FL3 | FL4 |
|---|---|---|---|---|---|---|
| 15 | 3000 | 150 | 212 | 608 | 1902 | 134 |
| 201 | 2520 | 163 | 253 | 666 | 2205 | 111 |
| 535 | 1852 | 125 | 195 | 582 | 1760 | 98 |

US 8,487,273 B2

MICROCHIP AND PARTICULATE FRACTIONAL COLLECTION APPARATUS

CROSS REFERENCE TO RELATED APPLICATION

The present application claims priority to Japanese Patent Application No. 2010-282167 filed on Dec. 17, 2010, the disclosure of which is incorporated herein by reference.

BACKGROUND

The present disclosure relates generally to microchips for collecting particulates and particulate fractional collection apparatuses provided with the microchips. More particularly, the disclosure relates to the microchip and the technology for fractionally collecting particulates subject to collection such as cells and micro-beads from a solution in which multispecies particulates are admixed.

Flow cytometry is an analytical method for examining and deciding the kind, size, structure, and so forth, of each of particulates which are flowing through channel in single line, by irradiating the particulates with excitation light such as laser light at a specific wavelength and by detecting the light emitted from the particulates, such as fluorescence and/or scattered light. In addition, based on the detection results obtained as mentioned above, it becomes feasible with the flow cytometry to fractionate intended particulates quickly and reliably even if multispecies particulates are contained in a sample liquid, by separating the intended particulates from other particulates based on the detection results obtained as mentioned above, and by collecting the particulates (for example, see "FLOW CYTOMETRY AT WILL" (Second Ed.) supervised by Hiromitsu Nakauchi, as Experiment Protocol Series of Cell Engineering Supplement, Shujunsha Co., Ltd., Aug. 31, 2006).

As the method of the fractional collection, there are utilized in general the charged droplet method configured to electrically charge droplets containing particulates, and the cell capture method configured to collect particulates with water streams using tubes. However, apparatuses adapted to these methods tend to be large in size and cost, and this gives rise to a problem of less versatility. In addition, in the fractionating method of forming droplets such as the charged droplet method, since the mechanism of droplet formation is sensitive to physical properties of liquid such as surface tension and viscosity, there encountered is another problem of causing the variation in the frequency of droplet formation and in the size of the droplets, affected by the change of measurement conditions.

Furthermore, in the fractionating method of forming droplets, since foreign matters are deposited on an ejection nozzle, thereby possibly varying the direction of droplet ejection, it is necessary to operate the system while readjusted frequently by a skilled worker. In addition, since incidental satellite (mist) generation inevitably occurs even if the droplet formation system is operating stably, that may result in not only failing the collection of intended cells, but also scattering cells in the surroundings.

Consequently, the methods of using microchips have been proposed recently, in which the microchips are each provided with minute channels formed in a substrate of either inorganic material such as silicone, glass, and so forth; or polymer material such as plastic and so forth (see the undermentioned Patent Documents 1 through 6, for example). As an example, WO 2005/121767, as Patent Document 1, discloses the technique of guiding a sample utilizing dielectrophoretic force so that the sample flowing through a main flow path in a microfluidic device is guided to a predetermined flow path. In the analytical fractionating apparatus disclosed in this Patent Document 1, the dielectrophoretic force is generated by providing multiple electrodes around the circumference of the main flow path in the microfluidic device and applying ac voltages to the electrodes.

On the other hand, Japanese Unexamined Patent Application Publications No. 2003-274924 and 2004-113223, as Patent Documents 2 and 3, respectively, disclose the technique of guiding cells to a predetermined branch flow path using an electroosmotic pump provided inside a microchip. In the cell separation apparatus disclosed in each of Patent Documents 2 and 3, the electroosmotic pump is provided on the chip, and intended cells are guided to a specific flow path by operating the electroosmotic pump. In addition, in Japanese Unexamined Patent Application Publications No. 2006-29824 and 2007-330201, as Patent Documents 4 and 5, respectively, the technology is disclosed of moving desired cells to a channel for cell fractionation with an optical tweezers utilizing laser light.

Furthermore, in Japanese Unexamined Patent Application Publication (Translation of PCT Application) No. 2005-538727, as Patent Document 6, the technology is disclosed of leading particulates to a predetermined branch flow path using an actuator. FIGS. 1A and 1B are sectional views schematically illustrating the operation in sequence of the steps carried out in the microfluidic system described in Patent Document 6. As shown in FIGS. 1A and 1B, in the microfluidic system described in Patent Document 6, a pair of sealed chambers, 102a and 102b, are provided adjacent to a flow path 101. The sealed chambers 102a and 102b are each connected to the flow, path 101 at a location immediately before junction point 101a through side paths 103a and 103b. In addition, a meniscus is formed in each of the side paths 103a and 103b with some of the liquid flowing into the side paths out of the liquid flowing through the flow channel 101.

When fractionating a particulate 104a by the microfluidic system, as shown in FIG. 1A, the sealed chamber 102a is pressed by an actuator 105 according to the timing of the particulate 104a arriving at the location leading to the side paths 103a and 103b. The liquid in the side path 103a is thereby pushed out toward the flow path 101, the flowing position of the particulate 104a is deflected in the direction of the side path 103b, and also the meniscus in the side path 103b is displaced in the direction of the sealed chamber 102b.

Subsequently, as shown in FIG. 1B, after the particulate 104a flows through passing the location connected to the side paths 103a and 103b, the pressing force by the actuator 105 is released, and the location of the meniscus in each of the side paths 103a and 103b is brought back to the previous location. As a result, the particulates 104b other than those subjected to collection, are made to flow through in the middle of the flow channel 101 and into a branch channel 106 subsequently, while only the particulates 104a subjected to the collection can be led to flow into a branch channel 107.

SUMMARY

In the abovementioned methods previously known, however, there encountered several problems as described herein below. Namely, in the analytical fractionating apparatus disclosed in Patent Document 1, since the particulates are displaced in the direction different from that of the liquid flow, the particulates have to be exerted by relatively strong force. As a result, the particles subject to collection tend to be suffered from damage with relative ease, and especially when the particulates are biological materials such as cells, this may cause a problem as the death of the cells.

As for this difficulty, although it is possible according to the techniques disclosed in Patent Documents 2 and 3, to carry out the collection without exerting electric stimuli to the cells, there encountered is another problem that the detection at high speed and high precision is not achieved since the electroosmotic pump is used for generating the force for driving the liquid, and sheath flows are not formed either. Even if the sheath flows are formed with the microchip described in Patent Documents 2 and 3, the difficulty still persists, in a manner similar to the case of Patent Document 6 mentioned later, in that either the cells may collide to the branch portion of flow path, thereby suffering from damage, or additional condensing works may become necessary because of low cell concentration in the liquid collected.

In addition, although the damage to particulates may be minor in the method using the optical tweezers, there is another difficulty in that the optical tweezers do not capture fast moving particulates. Therefore, in the method described in Patent Documents 4 and 5, the intended particulates are not fractionated unless the liquid flow is halted, thereby resulting in poor workability. Furthermore, since an optical system for scanning and irradiating laser light is necessary in the method using the optical tweezers described in Patent Documents 4 and 5, this gives rise to another problem with the method that its apparatus becomes complicated in structure and large in size.

In the method disclosed in Patent Document 6, on the other hand, since the particulates subject to collection are guided to a collection flow path by exerting fluidic forces to the particulates by control flows, and displacing the particulates onto the stream lines which are flowing into the collection flow path, there encountered is a problem that condensing works and so forth become necessary since the cell concentration in the collected liquid is low. When forming sheath streams, the volume of sheath liquid flux to be fed is usually relatively large compared with the flux of sample liquid, and accurate detection is carried out by squeezing the sheath liquid flux to have a small cross-sectional at the location of detection unit, thereby forming sheath streams with less variation of particulate position.

The ratio of the flux of sample liquid to that of sheath liquid can be obtained by assuming laminar flows to have parabolic velocity distribution at the detection unit. For example, in order to obtain a cross-section of sample stream of approximately 10 μm in diameter at the detection unit which is formed having a cross-section of 200 μm squares, the ratio, (flux of sheath liquid):(flux of sample liquid), is obtained as approximately 250:1. In this case, with particulate fractionating apparatus using the flow chip of such construction as described in Patent Document 6, both sheath liquid and sample liquid are constantly flowing during operation, these liquids are distributed after branching according to inverse ratio of each flow resistance, and disposed from each of exhaust ports by way of individual branch channel.

When carrying out the detection and collection of particulates contained in a 1 ml sample liquid, following the above example (detection flow channel of 200 μm squares crosssection, and sample stream cross section of 10 μm in diameter), the amount of the sheath liquid is estimated to be approximately 250 ml. Furthermore, supposing the flow resistance after branching for the collection flow channel and the disposal flow channel to be 3:2, the flux ratio is then obtained to be 2:3, and this give the amount of the sheath liquid disposed from the collection flow channel to be approximately 100 ml. That is, even if all the 1 ml sample liquid is recovered from the collection flow channel, this comes to indicate that the sample liquid is already diluted to about 100 times in the collected liquid.

In addition, if the particles subject to collection are living cells, the operations of condensation and so forth are necessary to properly utilize the living cells, and these works are not only cumbersome, but may also cause a problem of damaging the cells. Especially, this poses a serious problem when the particulates to be collected are merely a tiny fraction among the total number of particles. For example, when collecting hematopoietic stem cells from bone marrow cells of an adult mouse, the hematopoietic stem cells are contained only about one cell in the bone marrow cells numbered in the range between $10^4$ and $10^5$, and, from the restrictions for stable pumping and so forth, the sample liquid is usually prepared at the cell concentration in the range approximately between $10^5$ and $10^7$ pieces in 1 ml. Therefore, the cell concentration in the collected liquid is diluted into the range approximately between 1 and 1000 pieces in 100 ml, and the condensation itself of the liquid becomes difficult, as a result.

In addition, there encountered is still another problem in the method described in Patent Document 6 that the particulates may pass near the wall surface of the channel, and that it is highly likely for the particulates subject to collection to collide with the wall surface at a high speed at the branch portion of flow path. In particular, when the particulates are living cells, being easy to be suffered from damage, there is possibly fear of causing from the collision with the wall surface, the death of cells to be collected. Therefore, the method described in Patent Document 6 is not suitable for collecting biological materials such as cells without causing damage.

The present disclosure addresses the foregoing and other problems associated with previous methods. It would be desirable, therefore, to provide microchips and particulate fractional collection apparatuses, capable of fractionally collecting particulates without causing damage to the particulates subject to collection.

The microchip according to the present disclosure is provided including a sample liquid feed channel for permitting a sample liquid containing at least a particulate to flow through; at least one pair of sheath liquid feed channels configured to merge to the sample liquid feed channel from both sides thereof for permitting a sheath liquid to flow through surrounding the sample liquid; a merging channel connected to the sample liquid feed channel and the at least one pair of the sheath liquid feed channels, for permitting the sample liquid and the sheath liquid to merge and flow through the merging channel; a vacuum suction unit connected to the merging channel, for absorbing and drawing into the particulate subject to collection; and at least one pair of discharge channels formed on both sides of the vacuum suction unit for permitting to flow through from the merging channel.

The vacuum suction unit included in the microchip may additionally be provided with a suction channel formed coaxially with the merging channel, a pressure chamber formed midway through the suction channel, and an actuator configured to operate only during collecting the particulate so as to increase the volume of the pressure chamber by a certain amount.

In this case, a piezoelectric element may be used as the actuator, for example.

Alternatively, the vacuum suction unit may be provided with a suction channel formed coaxially with the merging channel, a pressure chamber formed midway through the suction channel, and an electroosmotic pump formed in the pressure chamber.

In addition, the width of the suction channel may be smaller than that of the merging channel, and larger than that of a sample stream.

In this case, the cross section in the flow direction of the suction channel may be smaller both in width and depth than that of the merging channel, and larger than that of the sample stream.

Furthermore, the microchip may be formed by bonding two substrates, and it is preferable in this case that at least the sample liquid feed channel, a portion of the merging channel, the suction channel, and the pressure chamber, are formed only on one of the substrates.

A particulate fractional collection apparatus according to the present disclosure is provided with the microchip mentioned above.

The fractional collection apparatus includes a light irradiation unit configured to irradiate a particulate flowing through the merging channel, with excitation light; a detection unit configured to detect scattered light and/or fluorescence emitted from the particulates; and a control unit configured to control the vacuum suction unit in the microchip based on detection results obtained by the detection unit.

In addition, in the case where the driving source of the vacuum suction unit is the piezoelectric element, the control unit may conduct the control of the drive of the vacuum suction unit with step signals.

Alternatively, in the case where the driving source of the vacuum suction unit is an electroosmotic pump, the control unit may conduct the control the drive of the vacuum suction unit with rectangular pulse signals.

In addition, the particulates can be fractionally collected according to the sequence of detection implemented by the detection unit to subsequently be stored in a row retaining the sequence in the vacuum suction unit.

Still in addition, based on the data obtained by the detection unit, the control unit may conduct the sequential control of the first process of drawing the particulate into the vacuum suction unit and the second process of taking the particulate out of the microchip, the particulate being previously drawn into the vacuum suction unit.

According to the present disclosure, since only the particulates subject to collection are drawn and collected, the particulates can be fractionally collected without suffering from damage, at high speed, with high stability, and reducing the dilution with the sheath liquid to the minimum.

Additional features and advantages are described herein, and will be apparent from the following Detailed Description and the figures.

BRIEF DESCRIPTION OF THE FIGURES

FIGS. 4A and 4B are perspective views illustrating the branch portion of the vacuum suction unit and the discharge channels included in the microchip shown in FIG. 2, while

FIG. 16A is a perspective view illustrating the construction of the electric double layer formation part, while

DETAILED DESCRIPTION

Figure 1A:
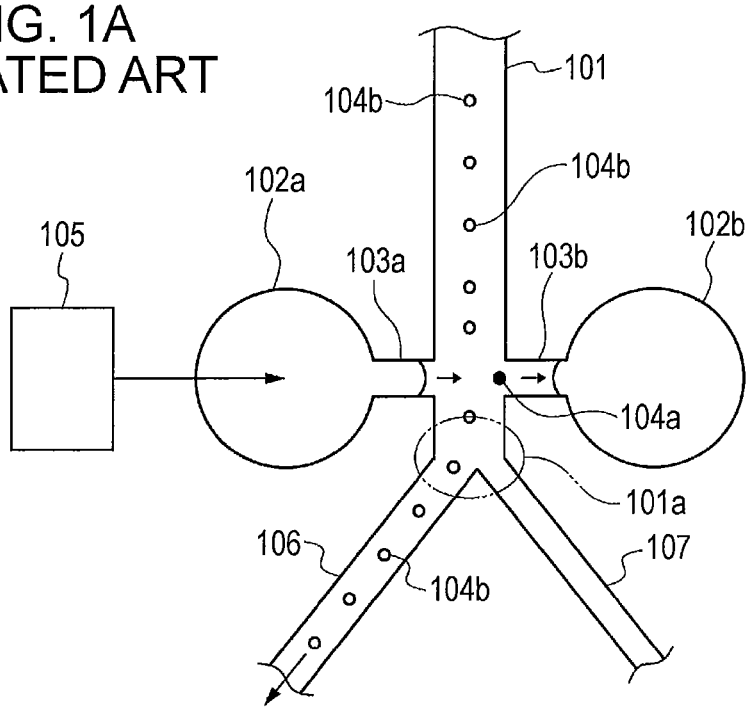
FIGS. 1A and 1B are sectional views schematically illustrating the operation in sequence of the steps carried out in the microfluidic system described in Patent Document 6.
Figure 1B:
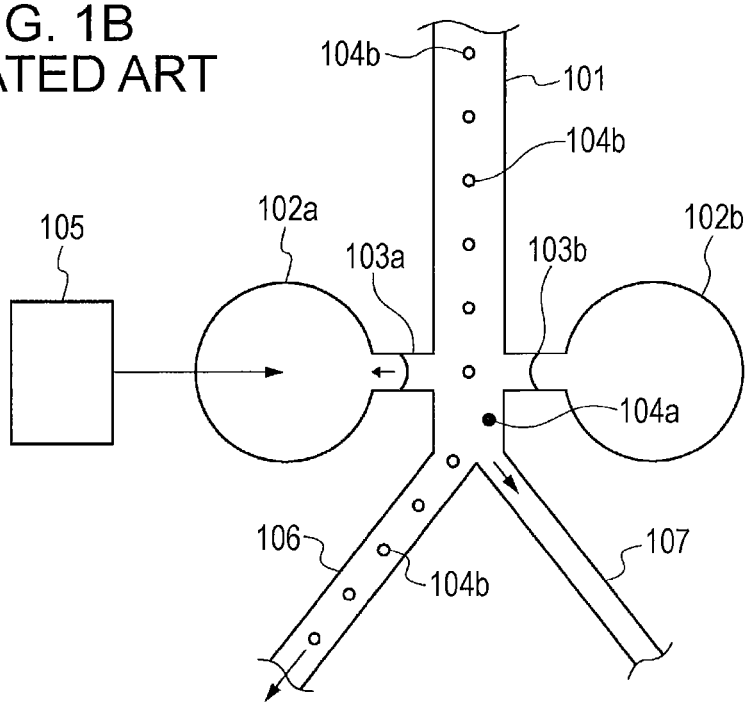

Embodiments of the present application will be described below in detail with reference to the drawings.

Referring now to the drawings, preferable embodiments for implementing the present disclosure is detailed hereinbelow. It is noted the following description is intended to be illustrative but not liming the present disclosure to the form disclosed herein. In addition, the description will be made in the following order.

1. First Embodiment
(Example of a microchip provided with a vacuum suction unit.

2. Modification to the First Embodiment
(Example of a microchip provided with a detection channel and a suction channel in the vacuum suction unit having the same depth with each other.)

3. Second Embodiment
(Example of a microchip including the vacuum suction unit additionally provided with a branch channel for fractionation.)

4. Third Embodiment
(Example of a particulate fractional collection apparatus provided with the microchip of the first embodiment.)

5. Fourth Embodiment
(Example of a microchip using an electroosmotic pump serving as actuator.)

<1. First Embodiment>
[Overall Construction of Microchip]

Figure 2:
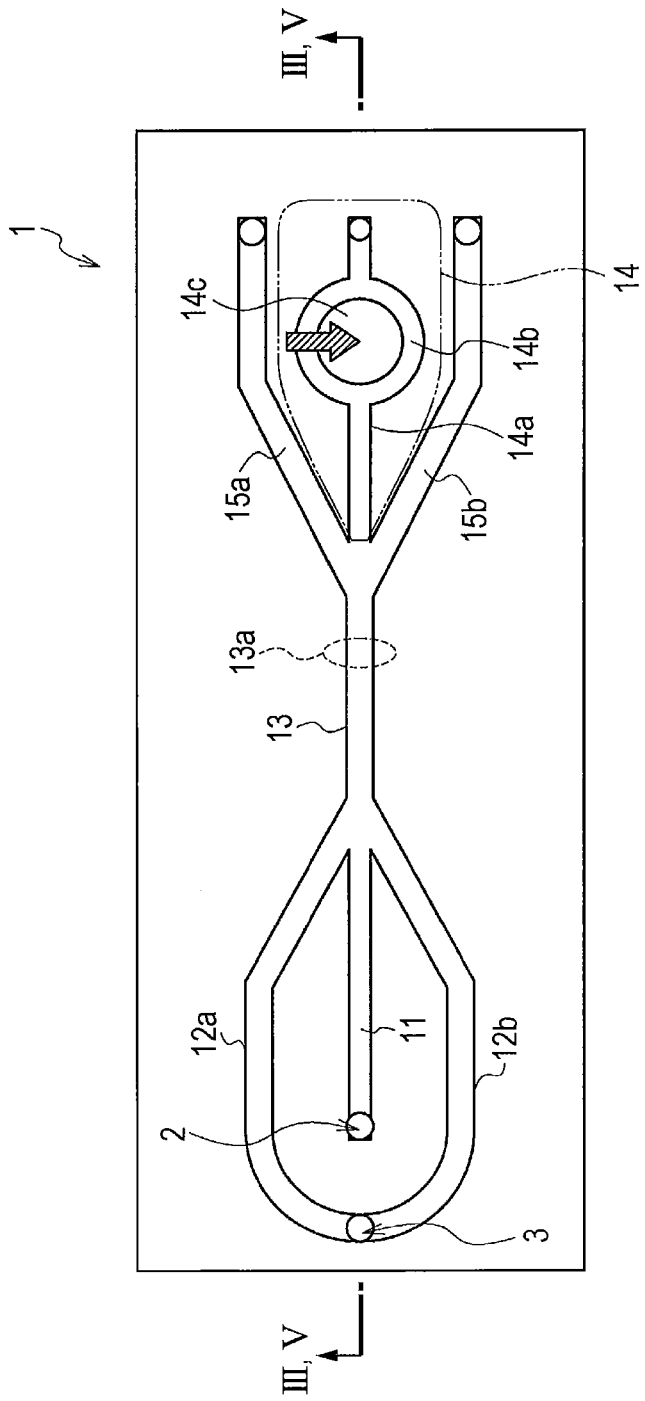
FIG. 2 is a sectional view schematically illustrating the construction of the microchip according to the first embodiment of the present disclosure.
Figure 3:
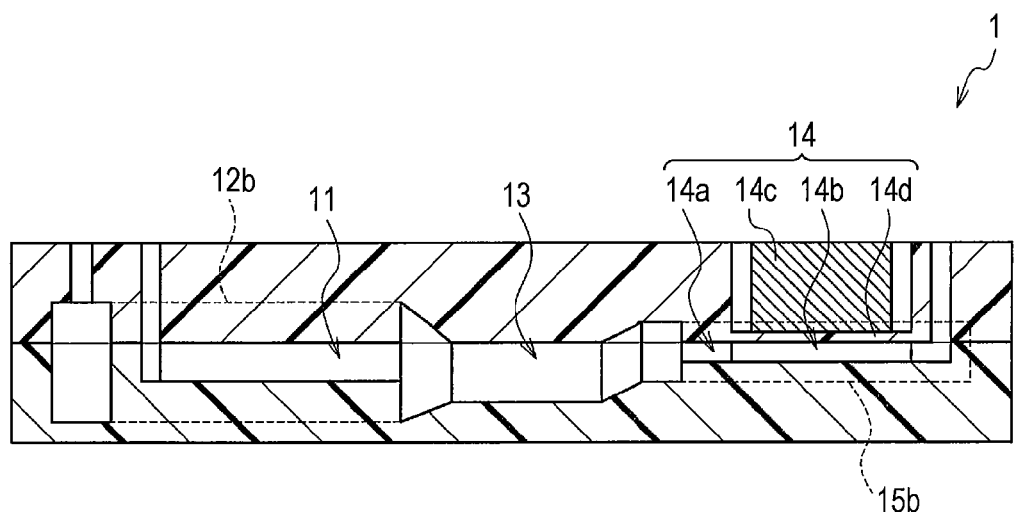
FIG. 3 is a sectional view taken along the line III-III of the structure shown in FIG. 2.

In the first place, a microchip will be explained according to a first embodiment of the present disclosure. FIG. 2 is a sectional view schematically illustrating the construction of the microchip according to the first embodiment, and FIG. 3 is a sectional view taken along the line III-III of the structure. As shown in FIGS. 2 and 3, the microchip 1 of this embodiment is provided with a sample liquid feed channel 11 configured to introduce a sample liquid 2 containing at least particulates, and one pair of sheath liquid feed channels, 12a and 12b, configured to introduce a sheath liquid 3.

The pair of sheath liquid feed channels, 12a and 12b, are arranged to merge from both sides of the sample liquid feed channel 11 so that one merging channel 13 is formed downstream from the point of the merger. Inside the merging channel 13, there is created the situation for the liquid to flow through in the form of laminar flow of sample streams 2a surrounded by sheath streams 3a. As a result, particulates contained in the sample liquid 2 come to flow through being arranged approximately in a column in the direction of the flow.

On the other hand, there provided in the downstream end portion of the merging channel 13 are a vacuum suction unit 14 configured to perform the fractionation of particulates subject to collection, and discharge channels 15a and 15b configured to dispose other particulates other than the particulates subject to collection, in which the vacuum suction unit and discharge channels are connected to the merging channel 13. In addition, the end portions on the side downstream of the discharge channels, 15a and 15b, are connected to a waste fluid tank and so forth, for example. The microchip 1 disclosed herein is configured to detect each of the particulates in the merging channel 13, and base on the results of the detection, to draw only the particulates which are determined as subject to collection, into the vacuum suction unit 14, while particulates other than the particulates subject to collection are disposed through the discharge channels 15a and 15b.

[Vacuum Suction Unit 14]

As for the vacuum suction unit 14, although the structure thereof is not particularly limited as long as it has the capability of drawing particulates subject to collection at a predetermined timing, it is formed, as shown in FIG. 2, by including a suction channel 14a connected to the merging channel 13, a pressure chamber 14b formed as a portion of the suction channel 14a, and an actuator 14c capable of expanding the volume enclosed with the pressure chamber 14b at a predetermined timing. In addition, it is preferred that the end portions on the side downstream of the suction channel 14a is formed to be capable of opening or closing with a valve (not shown) and so forth, for example.

Figure 4A:
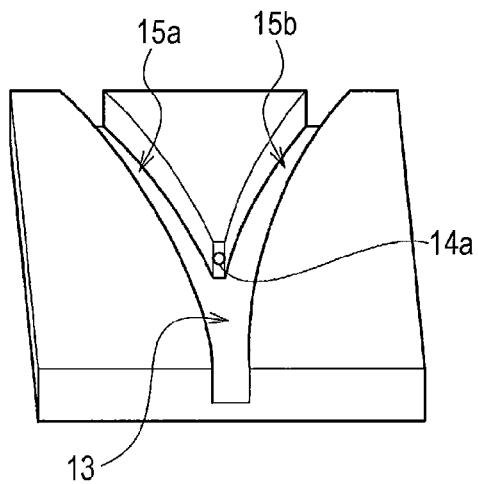
Figure 4B:
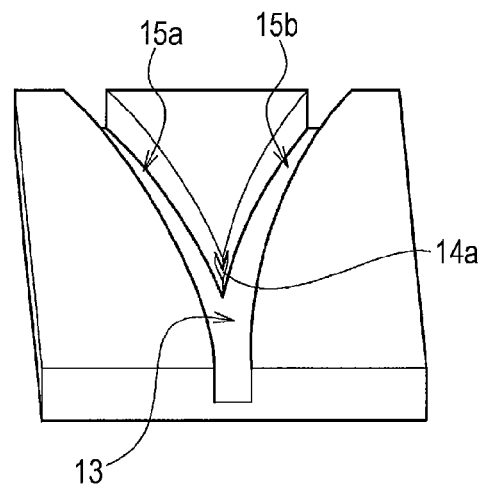
Figure 4C:
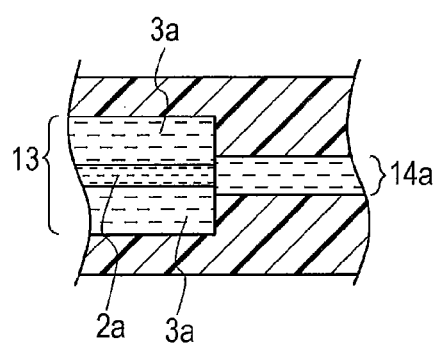
FIG. 4C is a sectional view illustrating the branch portion shown in FIGS. 4A and 4B.

FIGS. 4A and 4B are perspective views illustrating the branch portion of the vacuum suction unit 14 and the discharge channels 15a and 15b included in the microchip 1 shown in FIG. 2, and FIG. 4C is a sectional view of the branch portion. As shown in FIGS. 4A and 4B, the suction channel 14a is formed coaxially with the merging channel 13 so that the cross section of the suction channel in the direction of liquid flow is smaller in both width and depth than the merging channel, and larger than the section of sample stream 2a. As a result, it becomes feasible to collect the particulates subject to collection without causing any damage, while appropriately controlling the dilution of the collection liquid with the sheath liquid 3.

The pressure chamber 14b is connected to the actuator 14c such as a piezoelectric element and so forth, through a diaphragm 14d. On operating the actuator 14c, the diaphragm 14d is attracted toward the actuator 14c so that the volume of the pressure chamber 14b increases. It is desirable the diaphragm 14d is formed to be larger in thickness in the portion thereof fixed to the actuator 14c, while smaller in other portions not fixed to the actuator 14c. As a result, the bending portion of diaphragm having a smaller thickness as mentioned above can be deformed under relatively weak force, and can therefore be driven at a high speed.

Figure 5:
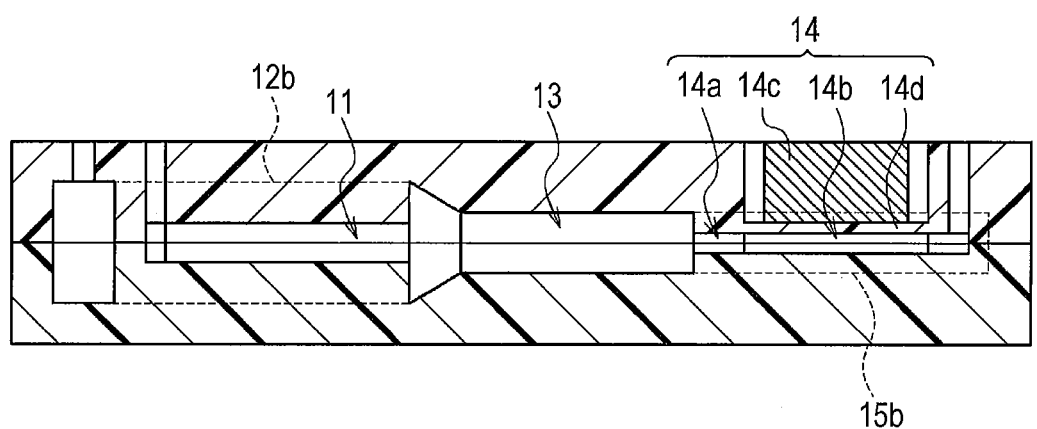
FIG. 5 is a sectional view illustrating another example of the microchip construction, which is equivalent to the sectional view taken along the line V-V of FIG. 2.

The microchip 1 of the present embodiment can be prepared as shown in FIG. 3, for example, by bonding two sheets of substrates in which each of the abovementioned channels and vacuum suction unit are formed. FIG. 5 is a sectional view illustrating another example of the microchip construction, which is equivalent to the sectional view taken along the line V-V shown in FIG. 2. Although the microchip 1 may be prepared as shown in FIG. 5 where each of the channels and vacuum suction unit are formed over both of two substrates, it is desirable to have the construction shown in FIG. 3 in which at least the sample liquid feed channel 11, a detection region 13a in the merging channel 13, the suction channel 14a, and the pressure chamber 14b are formed on only one of the substrates. As a result of adopting the above structure on which the portions having narrow channel diameters are formed only on one of the substrates, the positioning and alignment during the bonding process is facilitated.

As the materials suitable for forming the microchip 1, there cited are polycarbonate, cycloolefin polymer, polypropylene, PDMS (polydimethylsiloxane), glass, silicone, and so forth, for example. In particular, because of its excellent workability and capability of offering less expensive replication with molding machines, it is preferable to prepare with polymer materials such as polycarbonate, cycloolefin polymer, polypropylene, and so forth. By adopting thus mentioned structure formed by bonding plastic molding substrates, the microchip 1 can be manufactured at lower cost.

Since the droplet formation, which is implemented in the charged droplet method, is not carried out with the microchip 1 of the present embodiment, it is possible to collect target particulates within the system physically stable. In addition, since both the detection and fractionation can be carried out inside the microchip, this causes none of concern such as scattering mists, and the collection operations can be carried out safely from a viewpoint of biohazards as well. Furthermore, since the microchip 1 of this embodiment can be manufactured inexpensively, it can be used as disposable chips, and can therefore be adapted to the regenerative medicine and so forth in which the cell contamination is one of the concerns.

In case where a chip exchange is carried out to replace with the microchip 1 of this embodiment, it is not necessary to perform tedious adjustments which are usually necessary in the charged droplet method, such as adjusting the position of discharge nozzles, landing positions of droplets, and the position of recovery column, whereby the present microchip can be used with ease. Moreover, in the microchip 1 of this embodiment, since it is configured to draw particulates subject to collection into the suction channel 14a one piece at a time under negative pressure, the amount of the liquid drawn into the suction channel 14a with the particulate can be reduced to the minimum necessary. As a result, the dilution caused by the sheath liquid can be suppressed to the degree equivalent to the charged droplet method.

In addition, since the suction channel 14a in the microchip 1 of this embodiment is formed coaxially with the merging channel 13, that is, in such a position as to easily permit the flow of the sample stream 2a, the particulates subject to collection are drawn into the suction channel 14a without touching the surface of channel wall. As a result, the damage to particulates can be minimized.

Still in addition with the microchip 1 of this embodiment, since the particulates drawn into the suction channel 14*a* are stored in a row according to the sequence of fraction, it is possible to be matched one to one with detection data stored in the system, for example. Then, it is also possible when collecting particulates from the suction channel 14*a*, to be taken out to the outside of the chip without disturbing the sequence previously stored as above. Incidentally, when there intended in the charged droplet method is the collection of particulates together with matching operation one to one with detection data, this is not practical since many collection columns are necessary for each of the particulates.

<2. Modification to the First Embodiment>

Figure 6A:
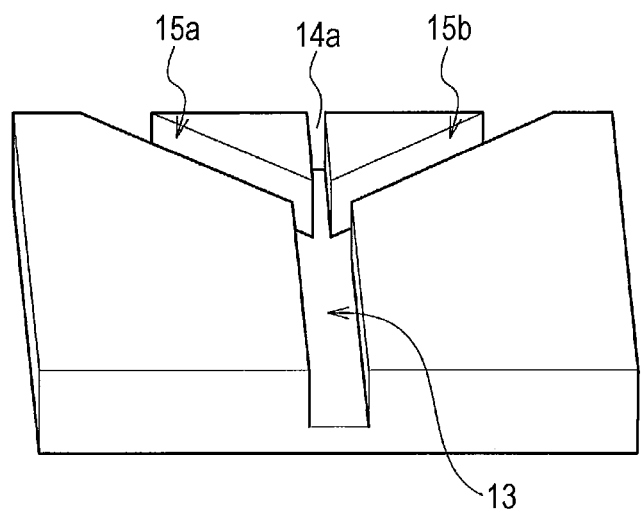
FIG. 6A is a perspective view illustrating the branch portion of the vacuum suction unit and discharge channels in the microchip according to a modification to the first embodiment of the present disclosure.
Figure 6B:
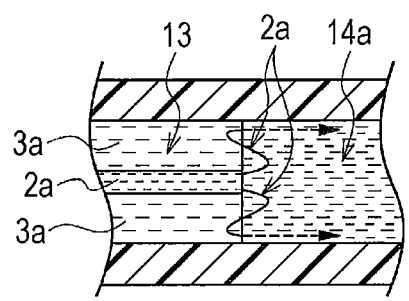
FIG. 6B is a sectional view illustrating trajectories of particulates in the branch portion.

In the above-mentioned first embodiment, the cross section of the suction channel 14*a* in the liquid flow direction is formed smaller in both width and depth than that of the merging channel 13. However, the present disclosure is not limited to this structure, but may alternatively be made equal in depth to the merging channel 13. FIG. 6A is a perspective view illustrating the branch portion of the vacuum suction unit and discharge channels in the microchip according to a modification to the first embodiment of the present disclosure, and FIG. 6B is a sectional view illustrating trajectories of particulates in the branch portion.

Referring to FIG. 6A, in the microchip 10 according to this modification, although the suction channel 14*a* is also formed coaxially with the merging channel 13, the cross section in the flow direction is smaller only in width compared with that of the merging channel 13, and it is the same in depth. Even in the case where the depth of the suction channel 14*a* is thus formed to be equal to the merging channel 13, since the suction channel 14*a* is still formed in such an arrangement as to permit the sample stream 2*a* to flow through, particulates subject to collection can be drawn under negative pressure without causing any damage.

In addition, by adopting such a construction as the microchip 10 according to this modification, it becomes feasible to draw particulates subject to collection into the suction channel 14*a* without causing blockage. However, as shown in FIG. 6B, since some of the particulates, though slight in number, enter into the suction channel 14*a* and make circumfluence in the depth direction, thereafter flow through the discharge channels, 15*a* and 15*b*, it is noted that the stay time may become longer for particulates at the branch portion.

<3. Second Embodiment>

Figure 7:
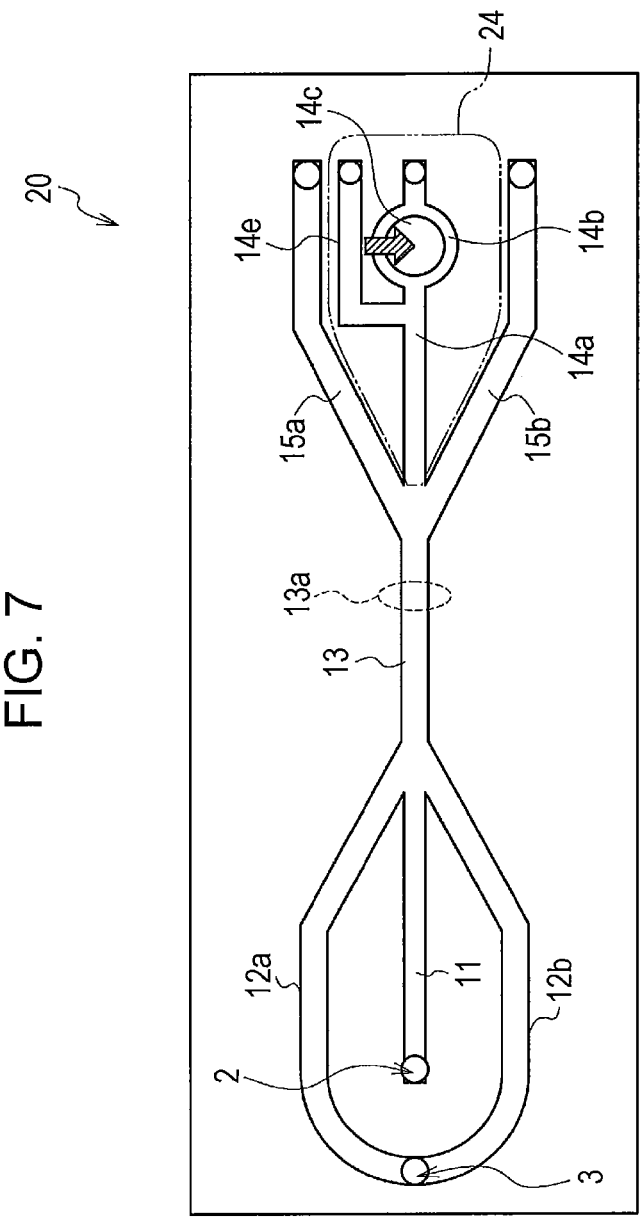
FIG. 7 is a sectional view schematically illustrating the construction of the microchip according to the second embodiment of the present disclosure.

In the next place, another microchip will be explained according to the second embodiment of the present disclosure. FIG. 7 is a sectional view schematically illustrating the construction of the microchip according to the second embodiment of the present disclosure. The components shown in FIG. 7 that are similar to those included in the microchip 1 of FIG. 2 are shown with the same reference numerals and the detailed description thereof is herein omitted. As shown in FIG. 7, the construction of the microchip 20 of the present embodiment is similar to the aforementioned first embodiment with the exception that a branch channel 14*e* for collecting particulates is additionally provided in a vacuum suction unit 24.

[Branch Channel 14*e*]

The branch channel 14*e* is configured to collect the particulates, which are drawn under negative pressure into the suction channel 14*a*, without flowing through the pressure chamber 14*b*, and is formed for the downstream end portion of the branch channel to be connected to an actuator (not shown) by way of a valve (not shown). When collecting particulates, the valve connected to the pressure chamber 14*b* is closed, the valve connected to the branch channel 14*e* for recovering particulates is opened, and then the actuator is activated. Since the particulates can be taken out according to these steps without flowing through the pressure chamber 14*b*, it becomes possible for the particulates be collected to be arranged in a column according to the sequence of fraction.

<4. Third Embodiment>

[Construction of Apparatus]

Figure 8:
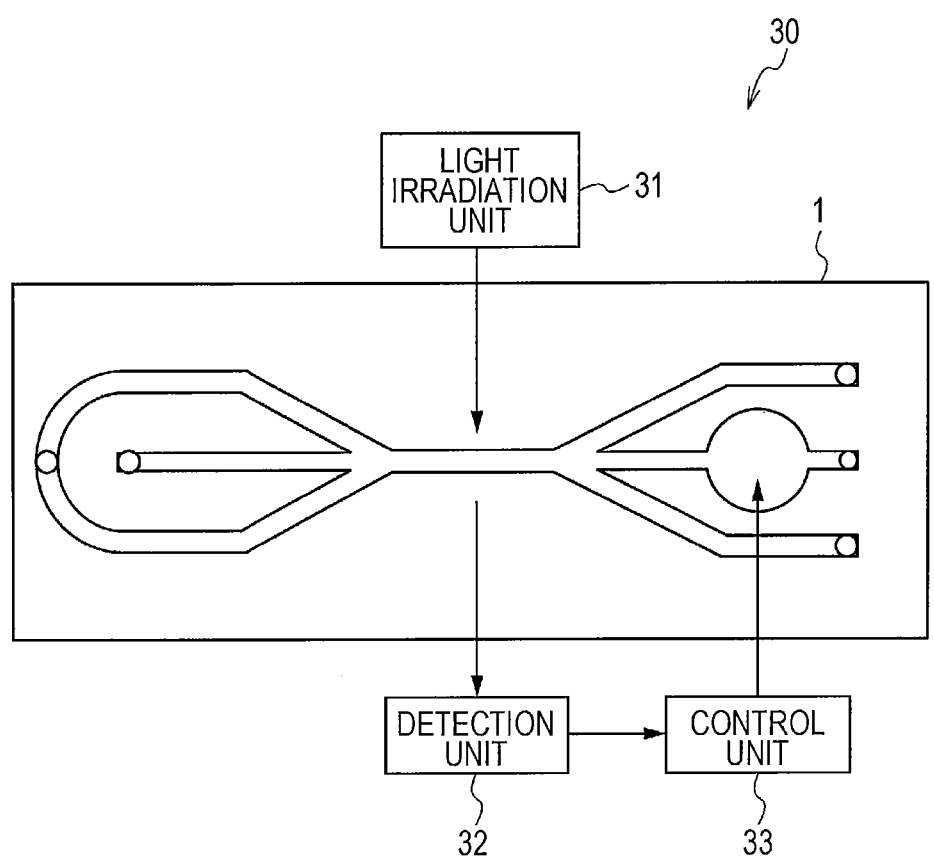
FIG. 8 is a sectional view schematically illustrating the construction of the particulate fractional collection apparatus according to the third embodiment of the present disclosure.

In the next place, a particulate fractional collection apparatus (hereinafter referred to simply as "fractionating apparatus", alternatively) will be explained according to the third embodiment of the present disclosure. FIG. 8 is a drawing schematically illustrating the construction of the particulate fractional collection apparatus according to the present embodiment. As shown in FIG. 8, the fractionating apparatus of the present embodiment is configured to collect specific particulates from a liquid containing a plurality of particulates using the aforementioned microchip 1 of the first embodiment, for example.

Specifically, the fractionating apparatus 30 according to the present embodiment is provided with a light irradiation unit 31 for irradiating particulates, which flow through the merging channel 13 in the microchip 1, with excitation light; a detection unit 32 for detecting the light emitted from the particulates irradiated with the excitation light; and a control unit 33 for controlling the vacuum suction unit 14 in the microchip 1 based on detection results obtained by the detection unit 32.

[Method of Fractionating Particulates]

Figure 9:
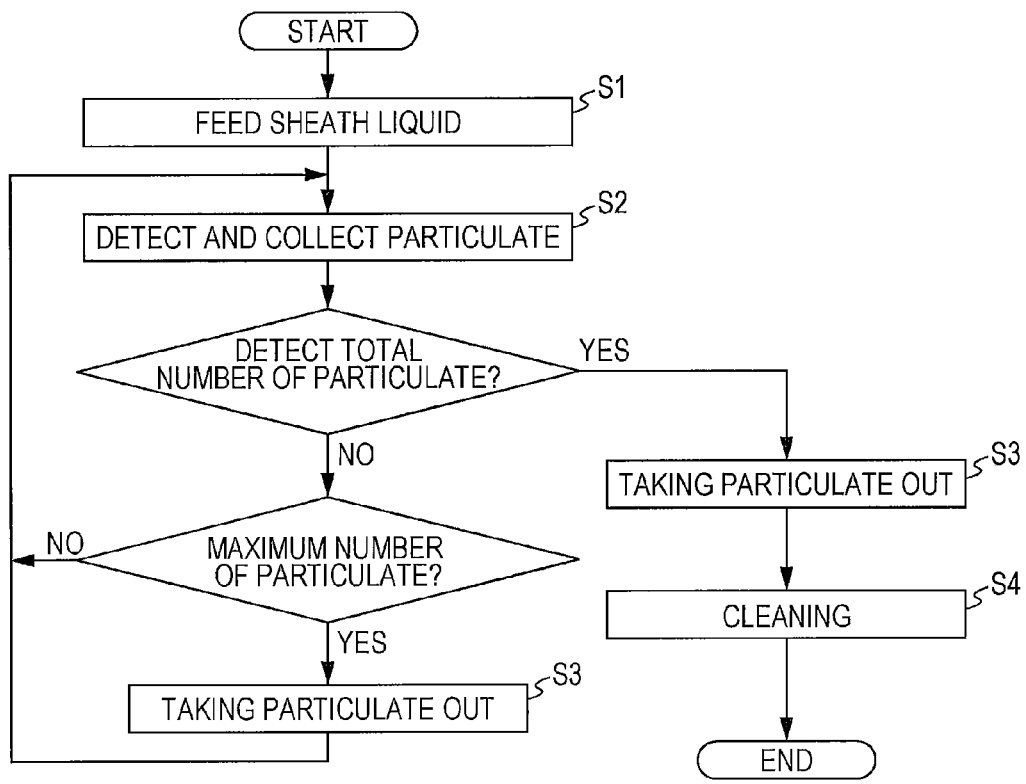
FIG. 9 includes a flow chart illustrating the method of fractionating particulates by the particulate fractional collection apparatus according to the third embodiment of the present disclosure.
Figure 10:
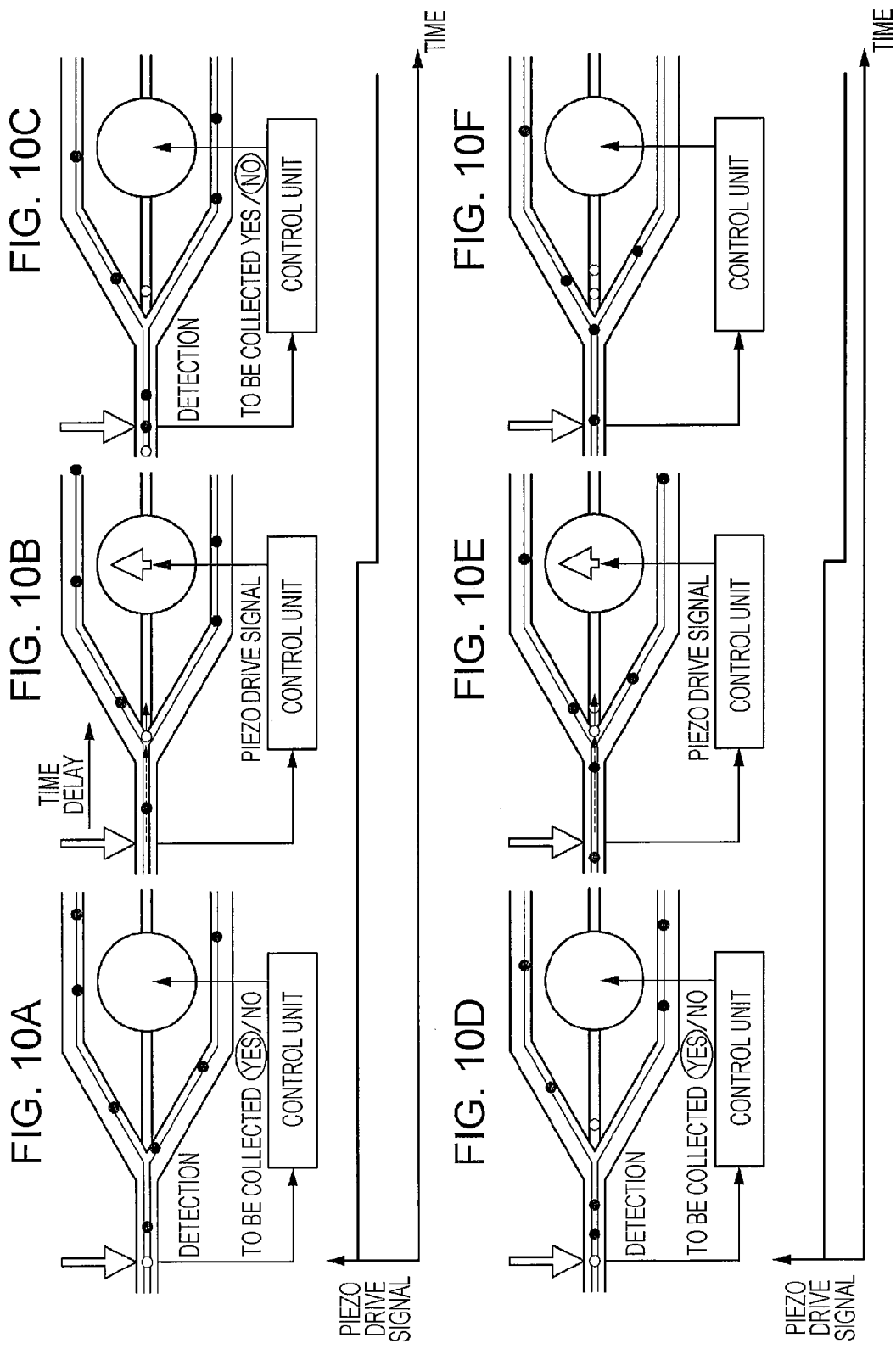
FIGS. 10A through 10F are sectional views illustrating the operation shown in FIG. 9 during the fractional collection of the particulates in sequence of process steps.

Next, there explained is the method of fractionating particulates with the particulate fractional collection apparatus 30 according to the present disclosure. FIG. 9 includes a flow chart illustrating the method of fractionating particulates according to the present embodiment. When fractionating particulates with the fractionating apparatus 30 of the present embodiment, the microchip 1 is first loaded in the apparatus. Thereafter, as shown in FIG. 9, a sheath liquid 3 is introduced into the sheath liquid feed channels, 12*a* and 12*b*, and the merging channel 13, the vacuum suction unit 14 (suction channel 14*a* and pressure chamber 14*b*) and the discharge channels, 15*a* and 15*b*, are filled with the sheath liquid 3 (step S1).

Subsequently, the downstream end portion of the suction channel 14*a* is closed with a valve, a sample liquid 2 is introduced together with a sheath liquid 3 to form a laminar flow, and the detection and collection of particulates are carried out (step S2). FIGS. 10A through 10F are sectional views illustrating the operation shown in FIG. 9 during the collection of the particulates in sequence of process steps. First at step S2, the particulates in the sample stream 2*a*, which are flowing through the merging channel 13, are irradiated with excitation light such as laser light at a wavelength of 488 nm, for example. Subsequently, the light emitted from the particulates, such as scattered light (forward scatter, backscatter) and/or fluorescence, are subjected to signal detection using a detector (photodetector, photomultiplier, or so forth) provided in the detection unit 32.

Thereafter, thus detected signals are subjected to pre-amplification if necessary, and subsequently sent to the control unit 33. In the control unit 33, it is then determined whether the particulate presently detected is a particulate subject to collection based on the detection signal. In the case where the thus detected particulate is decided as the particulate subject to collection, the signal is generated for driving the actuator 14*c* such as piezo element drive signal, in such a manner as illustrated in FIGS. 10A through 10F, after elapsing a certain time (delay time) which is necessary for the particulate to flow from the location irradiated with the excitation light to the location of the branch portion. In this case, it may alternatively be possible for the actuator 14c be driven through an amplifier, if necessary.

When a piezoelectric element is used as the actuator 14c, for example, since the piezo deformation force is generated by controlling piezo application voltages, thereby causing the change in the volume of the pressure chamber 14b, the inner pressure of the vacuum suction unit 14 can be controlled. Specifically, by applying such voltages as to induce the piezo contraction, increasing the volume of the pressure chamber 14b, and making the inner pressure of the chamber to be negative, the suction channel 14a operates to draw the particulate there into. The amount of suction in this case can be controlled by varying applied voltage.

In addition, when the piezoelectric element is used as the actuator 14c, the displacement of the piezoelectric element, i.e., the drive voltage applied to the element is directly related to the volume of the pressure chamber 14b. As a result, if the drive waveform is in the shape of inverting rectangular pulse, the particulate which is drawn into the suction channel 14a at the falling edge of the rectangular wave, may come to be discharged at the rising edge of the rectangular wave. Therefore, in order continuously to draw and accumulate the particulate into the suction channel 14a in case of the piezoelectric element, the waveform of input signal has to be in the shape of step.

According to the method of fractionating particulates according to the present embodiment, therefore, it becomes feasible to draw only the particulate to be collected in a stable manner. In addition, the dilution inside of suction channel 14a can be prevented by repeatedly drawing a minimum quantity into the channels, and particulates can be placed in sequence and stored in the order detected, as well. On the other hand, when particulates other than the particulate subject to collection are detected, it is enough not to drive the actuator 14c. The particulates other than the particulate subject to collection are thereby led to flow through the discharge channels, 15a and 15b, and disposed to the outside.

In the case where either the introduction of the total amount of sample liquid 2 is completed, or the number of the collected particulates reaches the collectable number for the microchip 1, the particulates are taken out of the microchip 1 (step S3). By the phrase mentioned herein above, "the case where the number reaches the collectable number for the microchip 1," is meant the case where either the suction flow channel is full with the particulates, or the movable range has reached its limit for the actuator 14c such as piezoelectric element, and so forth.

Figure 11:
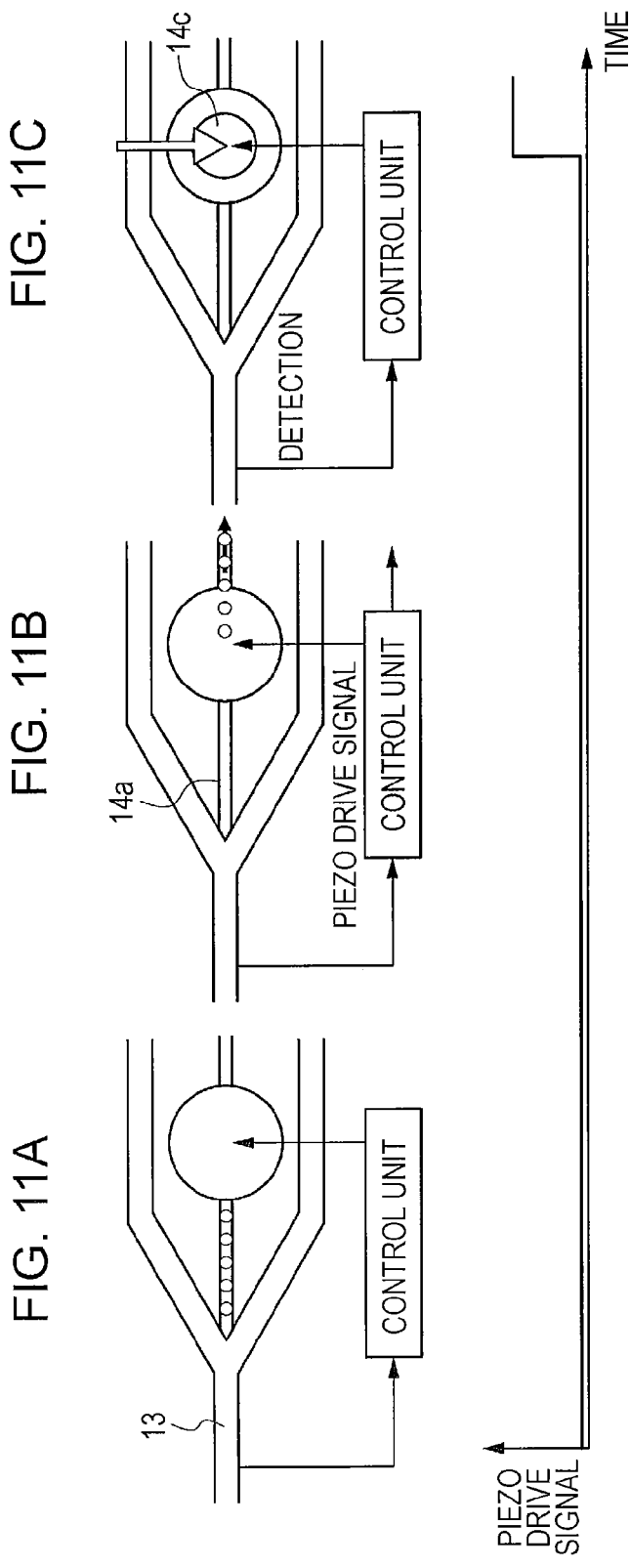
FIGS. 11A through 11C are sectional views illustrating the operation shown in FIG. 9 during taking the particulates out in sequence of process steps.

FIGS. 11A through 11C are sectional views illustrating the operation shown in FIG. 9 during taking the particulates out in sequence of process steps. First at step S3, as shown in FIG. 11A, under the conditions of the sheath liquid 3 being introduced, and the introduction of only the sample liquid 2 being interrupted, there realized is the absence of the sample liquid 2 (particulates) on the side upstream from the junction in the downstream end portion of the merging channel 13. Thereafter, as shown in FIG. 11B, the valve connected to the suction channel 14a is opened. Since the liquid currently stored in the suction channel 14a thereby flows out together with particulates by the supply pressure of the sheath liquid 3, the particulates subject to collection can be taken out to the exterior of the microchip 1.

Subsequently, as shown in FIG. 11C, after taking out the collected particulates entirely, the actuator 14c in the microchip 1 is brought back to the initial state. When the detection and collection have not been completed for the entire amount of sample liquid 2, the valve connected to the suction channel 14a is closed once again, the sample liquid 2 is introduced, and the detection and collection of particulates at the step S2 are performed.

On the other hand, when the detection and collection have been completed for the entire amount of sample liquid 2, after taking out the particulates at step S3, either the sheath liquid 3 or a cleaning fluid is introduced to both the sample liquid feed channel 11 and the sheath liquid feed channels, 12a and 12b, and the insides of flow paths are cleaned (step S4). Furthermore, a preservative liquid such as pure water may be introduced to replace the insides of the flow paths, if necessary.

Since droplets are not formed with the particulate fractional collection apparatus of the present embodiment, it is possible to collect particulates subject to collection inside the physically stable system. In addition, since both the detection and fractionation can be carried out inside the microchip, and causing none of concerns of scattering mists, the collection operations can be carried out safely. Furthermore, in the case of chip replacement in the particulate fractional collection apparatus of the present embodiment, it is not necessary to perform tedious adjustments that are usually necessary in the charged droplet method such as the position of discharging nozzles, landing positions of droplets, and the position of recovery columns, whereby work efficiency can be improved.

Figure 12:
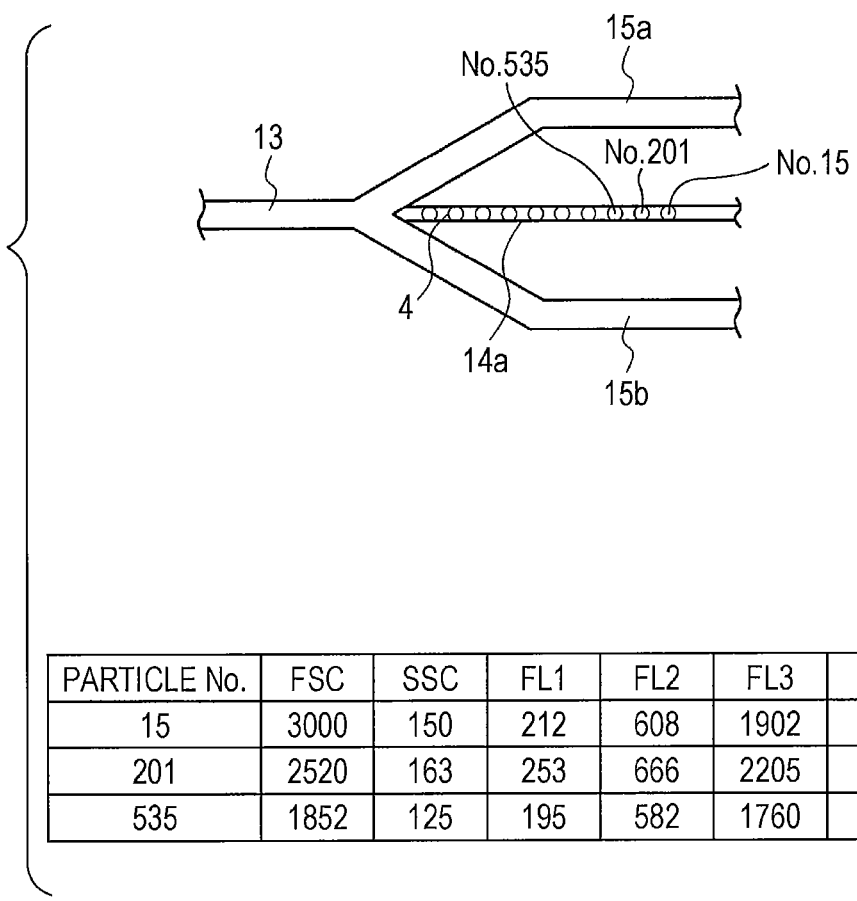
FIG. 12 is a drawing schematically illustrating the features of the system at the time of particulate collection.

With the particulate fractional collection apparatus of the present embodiment, since the concentration of particulates in the collection liquid is high, condensation operations can be reduced to minimum. As a result, the damage of particulates can also be suppressed. FIG. 12 is a drawing schematically illustrating the features at the time of particulate collection. As shown in FIG. 12, with the particulate fractional collection apparatus of the present embodiment, the particulates 4 are fractionated according to the sequence of the detection conducted by the detection unit 32, and stored in a row retaining the sequence in the suction channel 14a in the vacuum suction unit 14. As a result, it becomes feasible to be matched one to one to detection data stored in the system, for example. In addition, when taking the particulates out of the suction channel, it is possible to be retrieved to the outside of the chip without disturbing the sequence.

Figure 13:
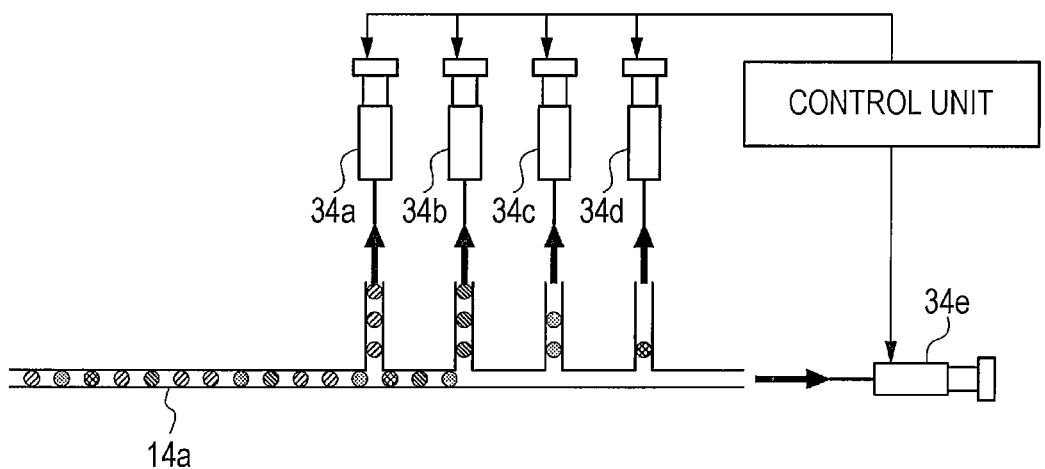
FIG. 13 is a drawing schematically illustrating an example of the method of fractionally collecting the particulates in the suction channel based on detection data.

Furthermore, with the particulate fractional collection apparatus of the present embodiment, it is also possible to collect the particulates by further fractionating once collected particulates according to the characteristics and so forth. FIG. 13 is a drawing schematically illustrating an example of the method of fractionally collecting the particulates in the suction channel 14a based on detection data. As shown in FIG. 13, since particulates are stored in a row in the suction channel 14a in the microchip 1 according to the sequence of the detection, the detection data can be correlated one by one to the particulates.

For example, by using particle collection actuators, such as syringe pumps 34a through 34e, and so forth, a specific particulate can be selected and taken out. Therefore, without tedious procedures, such as those necessary in the charged droplet method, it becomes possible to collect particulates of multispecies at once, and take out thereafter while further fractionating these particulates with relative ease.

On the other hand, as mentioned earlier, "the collectable number for the microchip 1" is determined by the chip design, and the number of particulates drawn into the suction channel 14a can be counted by the system. With the particulate fractional collection apparatus of the present embodiment, therefore, by properly setting "the collectable number for the microchip 1" in advance, several operations such as either repeating the steps S2 and S3, or all of the steps, S1 to S4, become feasible under the sequential control conducted by the control unit 33.

<5. Fourth Embodiment>

Figure 14:
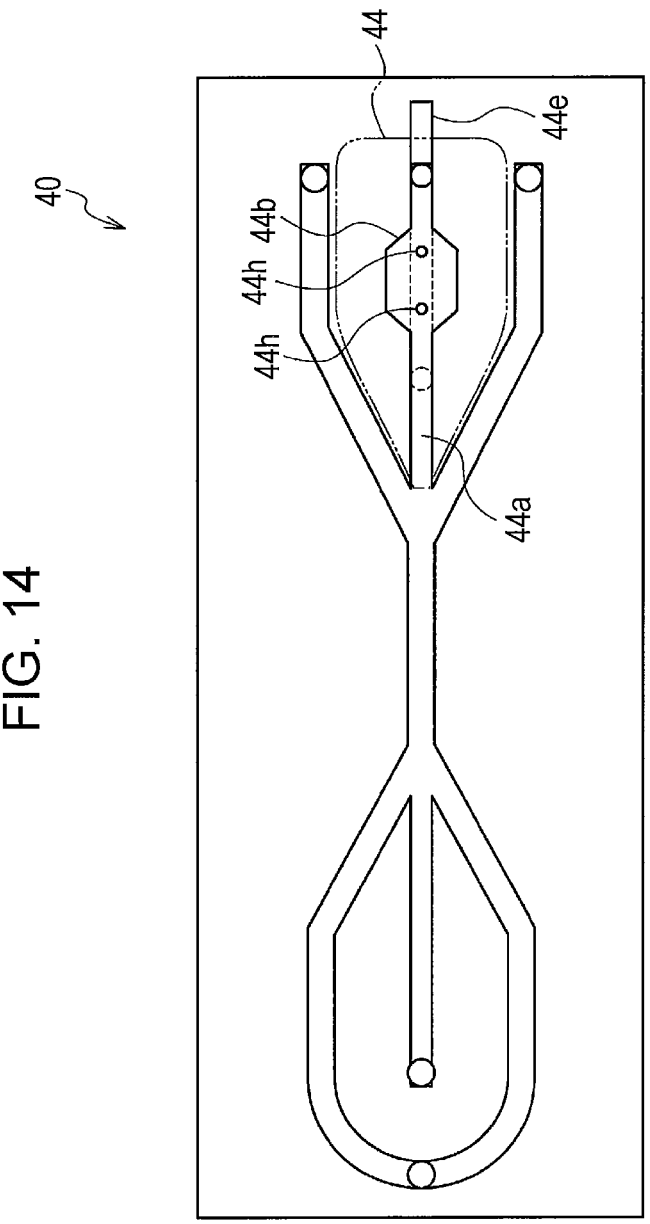
FIG. 14 is a sectional view schematically illustrating the construction of the microchip according to the fourth embodiment of the present disclosure.

In the next place, another microchip will be explained according to the fourth embodiment of the present disclosure. FIG. 14 is a drawing schematically illustrating the construction of the microchip of this embodiment. The components and units shown in FIG. 14 that are similar to those included either in the microchip 1 of FIG. 2 or in the microchip 20 of FIG. 7, are shown with the same reference numerals and the detailed description thereof is omitted. As shown in FIG. 14, the construction of the microchip 40 of the present embodiment is similar to the aforementioned second embodiment with the exception that an electroosmotic pump is additionally provided in the vacuum suction unit 44, as an actuator for increasing the volume of the pressure chamber by a certain amount.

[Vacuum Suction Unit 44]

Figure 15A:
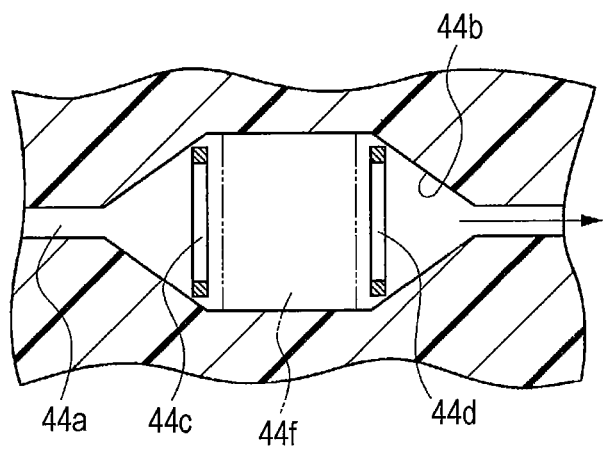
FIGS. 15A and 15B are sectional views illustrating the construction of the electroosmotic pump formed in the vacuum suction unit in the microchip shown in FIG. 14, showing the section perpendicular and parallel to the thickness direction, respectively.
Figure 15B:
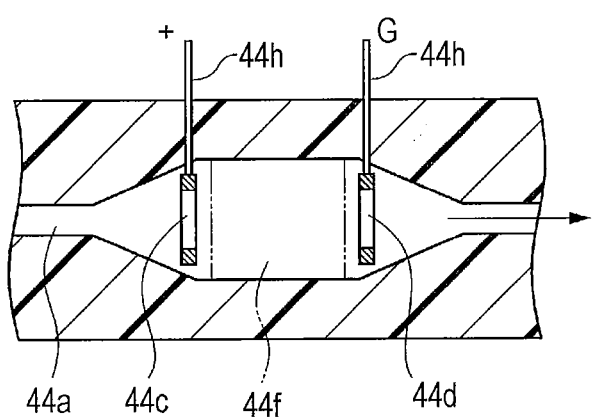

FIGS. 15A and 15B are sectional views illustrating the configuration of the electroosmotic pump formed in the vacuum suction unit 44 of the microchip 40 shown in FIG. 14, in which FIG. 15A shows the section perpendicular to the direction of thickness and FIG. 15B shows the section parallel to the thickness direction. The electroosmotic pump is provided inside the pressure chamber 44b formed as the portion of the suction channel 44a in the vacuum suction unit 44 of the microchip 40 of the present embodiment. Specifically, one pair of electrodes 44c and 44d are provided for forming an electric double layer with the liquid in the pressure chamber 44b. That is, the portion sandwiched between the electrodes 44c and 44d serves as an electric double layer formation part 44f.

Figure 16A:
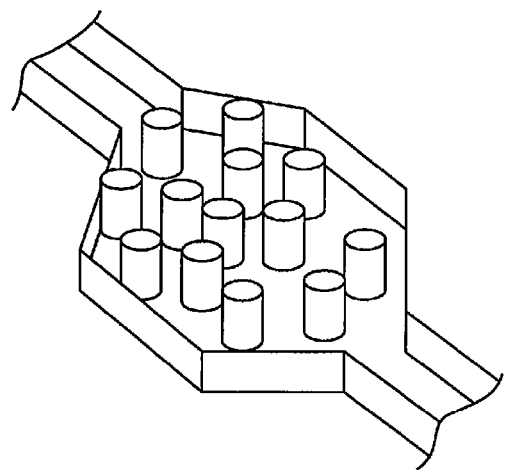
Figure 16B:
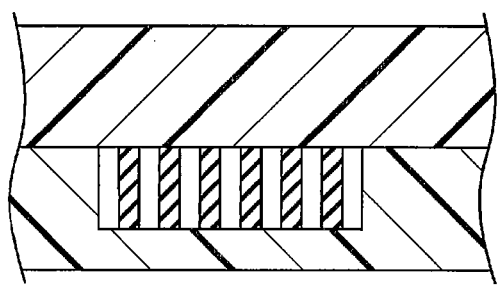
FIG. 16B is a sectional view thereof.

FIG. 16A is a perspective view illustrating the construction of the electric double layer formation part 44f, and FIG. 16B is a sectional view thereof. The construction of the electric double layer formation part 44f is not particularly limited, and may also be formed of porous silica members or with pillars which are densely arranged to convert the channel into an array structure as shown in FIGS. 16A and 16B, for example. In addition, the materials for forming solid members herein are not particularly limited, and may be formed with glass, silicon, or acryl, similarly to the chip formation. Furthermore, the materials may additionally be provided with surface treatment by $SiO_2$ sputtering method and so forth.

Although high driving pressures can be obtained by the aforementioned construction with porous silica members or micro channel structure for forming the electric double layer formation part 44f, it becomes difficult, on the other hand, to flow particulates through the pressure chamber 44b. Therefore, when adopting the structure such as those abovementioned for forming the electric double layer formation part 44f, it is necessary to provide a branch channel 44e separately for collecting particulates.

Figure 17A:
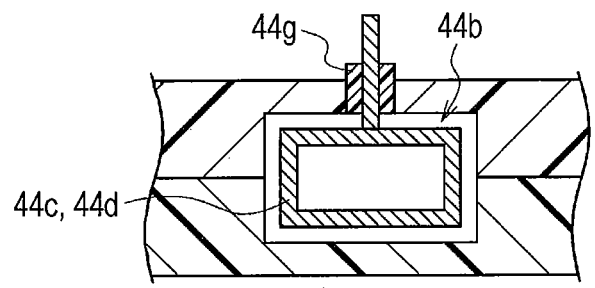
FIG. 17A through 17C are sectional views illustrating the exemplary construction of the electrodes.
Figure 17B:
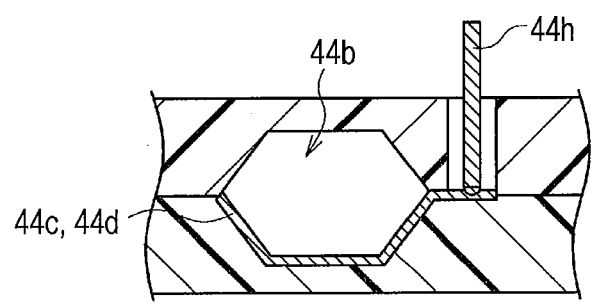
Figure 17C:
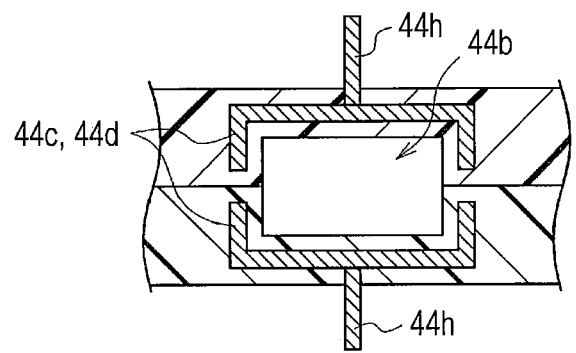

FIGS. 17A through 17C are sectional views illustrating the exemplary constructions of electrodes 44c and 44d formed in the vacuum suction unit of the microchip. The construction of the electrodes 44c and 44d is not particularly limited also, and may be formed as shown in FIG. 17A, for example, by preparing electrodes 44c and 44d formed as conductive laminated plates of gold, platinum, aluminum, and so forth; arranging the electrodes inside the pressure chamber 14b; forming the chip by bonding; and sealing with adhesives 44g.

In addition, as shown in FIG. 17B, the electrodes may be formed alternatively by preparing thin film electrodes 44c and 44d of metal such as gold, platinum, or aluminum, ITO (indium-tin oxide), and so forth, which are deposited by the sputtering method on the inner surface of the pressure chamber 44b; and by connecting a contact pin 44h thereto. Furthermore, as shown in FIG. 17C, electrodes 44c and 44d may be sealed during the preparation of the chip, and subsequently subjected to the solid casting.

Thereafter, by applying voltages in the flow direction under the conditions that the electric double layer has been formed, the displacement of liquid in the pressure chamber 44b takes place and the system serves as an electroosmotic pump. As for the direction of applying the voltages, in case where the solid surface is negatively charged such as for porous silica members, either a positive voltage is applied to the electrode 44c placed upstream of the flow direction, while grounding the electrode 44d placed downstream of the flow direction; or the electrode 44c is grounded, while a negative voltage is applied to the electrode 44d. By contrast, in case where the solid surface is positively charged, either the electrode 44c is grounded, while a positive voltage is applied to the electrode 44d; or a negative voltage is applied to the electrode 44c, while the electrode 44d is grounded.

Since the electroosmotic pump operates only when drive voltages are applied, thereby generating negative pressures, the waveform of input signals have to be rectangular pulses. This is for the reason that if the waveform of input signals is in the shape of step as adopted earlier in the case of the piezoelectric element, the pump comes to operate continuously drawing the liquid into the suction flow channel.

In addition, it is necessary to open the valve provided downstream of the electroosmotic pump (pressure chamber 44b) at least when the electroosmotic pump is on. Incidentally, when the electric double layer formation portion is formed with porous materials, since the porous materials have a large fluid resistance, the rate of the flow into the suction channel 44a is small even when the electroosmotic pump is off, and the flow rate into the suction channel 44a can further be suppressed by applying reverse bias voltages.

Since the suction of particulates is carried out with the electroosmotic pump formed in the microchip of the present embodiment, there lifted is the restriction of the aforementioned maximum displacement (maximum applied voltage) as in the case where the piezoelectric element is used. As a result, the fractionating microchip can be realized having the capability of achieving a large collectable particulate number in one operation. In addition, since the electroosmotic pump operates silent and vibration-free, this broadens the choice of the locations available. Incidentally, it is noted that the constructions and effects of the present embodiment other than the above-mentioned are similar to those described earlier according to the first and second embodiments.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A microchip, comprising:
   a sample liquid feed channel for permitting a sample liquid containing at least a particulate to flow through;
   at least one pair of sheath liquid feed channels configured to merge to the sample liquid feed channel from both sides thereof for permitting a sheath liquid to flow through surrounding the sample liquid;
   a merging channel connected to the sample liquid feed channel and the at least one pair of the sheath liquid feed channels, for permitting the sample liquid and the sheath liquid to merge and flow through the merging channel;
a vacuum suction unit connected to the merging channel, for absorbing and drawing into the particulate subject to collection; and
at least one pair of discharge channels formed on both sides of the vacuum suction unit for permitting to flow through from the merging channel.

2. The microchip according to claim 1, wherein the vacuum suction unit is provided with a suction channel formed coaxially with the merging channel, a pressure chamber formed midway through the suction channel, and an actuator configured to operate only during collecting the particulate so as to increase a volume of the pressure chamber by a certain amount.

3. The microchip according to claim 2, wherein the actuator is a piezoelectric element.

4. The microchip according to claim 2, wherein a width of the suction channel is smaller than that of the merging channel and larger than that of a sample stream.

5. The microchip according to claim 4, wherein a cross section in a flow direction of the suction channel is smaller both in width and depth than that of the merging channel, and larger than that of the sample stream.

6. The microchip according to claim 2, wherein the microchip is formed by bonding two substrates.

7. The microchip according to claim 6, wherein at least the sample liquid feed channel, a portion of the merging channel, the suction channel, and the pressure chamber are formed only on one of the substrates.

8. The microchip according to claim 1, wherein the vacuum suction unit is provided with a suction channel formed coaxially with the merging channel, a pressure chamber formed midway through the suction channel, and an electroosmotic pump formed in the pressure chamber.

9. A particulate fractional collection apparatus, the particulate fractional collection apparatus comprising the microchip according to claim 1.

10. The particulate fractional collection apparatus according to claim 9, further comprising:
a light irradiation unit for irradiating a particulate with excitation light, the particulate flowing through the merging channel;
a detection unit for detecting at least one of scattered light and fluorescence emitted from the particulates; and
a control unit for controlling the vacuum suction unit in the microchip based on detection results obtained by the detection unit.

11. The particulate fractional collection apparatus according to claim 10, wherein
a driving source of the vacuum suction unit is a piezoelectric element, and wherein
the control unit is configured to control a drive of the vacuum suction unit with a step signal.

12. The particulate fractional collection apparatus according to claim 10, wherein
a driving source of the vacuum suction unit is an electroosmotic pump, and wherein
the control unit is configured to control a drive of the vacuum suction unit with a rectangular pulse signal.

13. The particulate fractional collection apparatus according to claim 10, wherein
the particulates are fractionally collected according to a sequence of detection implemented by the detection unit to be subsequently stored in a row retaining the sequence in the vacuum suction unit.

14. The particulate fractional collection apparatus according to claim 10, wherein
a sequential control of a first process and a second process is conducted by the control unit based on data obtained by the detection unit, the first process being a process of drawing the particulate into the vacuum suction unit, and the second process being a process of taking the particulate out of the microchip, the particulate being previously drawn into the vacuum suction unit.

* * * * *